United States Patent [19]

Myers et al.

[11] Patent Number: 5,476,851

[45] Date of Patent: Dec. 19, 1995

[54] PYRAZOLO[3,4-G]QUINOXALINE COMPOUNDS WHICH INHIBIT PDGF RECEPTOR PROTEIN TYROSINE KINASE

[75] Inventors: Michael R. Myers, Reading; Paul E. Persons, King of Prussia; Cuong Q. Ly, Collegeville; Alfred P. Spada, Lansdale, all of Pa.

[73] Assignee: Rhone-Poulenc Rorer Pharmaceuticals, Inc., Collegeville, Pa.

[21] Appl. No.: 303,097

[22] Filed: Sep. 8, 1994

[51] Int. Cl.$^6$ ..................... A61K 31/495; C07D 237/26
[52] U.S. Cl. ........................................... 514/250; 544/345
[58] Field of Search .............................. 514/250; 544/345

[56] References Cited

U.S. PATENT DOCUMENTS

| | | | |
|---|---|---|---|
| 4,954,498 | 9/1990 | Mertens et al. | 514/254 |
| 5,075,306 | 12/1991 | Jacobsen et al. | 514/250 |

OTHER PUBLICATIONS

Venugopalan et al., Indian Journal of Chemistry, 29B, Apr. 1990, pp. 364–365.

*Primary Examiner*—Mukund J. Shah
*Assistant Examiner*—Matthew V. Grumbling
*Attorney, Agent, or Firm*—James A. Nicholson; Raymond S. Parker, III; Martin F. Savitzky

[57] ABSTRACT

This invention relates to pyrazolo[3,4-g]quinoxaline compounds exhibiting protein tyrosine kinase inhibition activity of the formula:

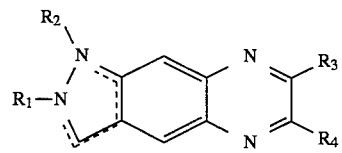

where:
- ----- may be a double bond;
- R, $R_2$, $R_3$ and $R_4$ are as described in claim 1;
- a pharmaceutically acceptable salt thereof.

More specifically, compounds of this invention are novel as selective inhibitors of the PDGF-R protein tyrosine kinase and can be applied as potential therapeutic agents for various disease states which are characterized by uncontrolled cellular proliferation. Further, the present invention provides pharmaceutical compositions and a method for treating such disorders comprising the administration to a patient of a PDGF receptor inhibiting effective amount of a pyrazolo[3,4-g]quinoxaline compound exhibiting protein tyrosine kinase inhibition activity. Processes for the preparation of pyrazolo[3,4-g]quinoxaline compounds are also described.

24 Claims, No Drawings

PYRAZOLO[ 3,4-G] QUINOXALINE COMPOUNDS WHICH INHIBIT PDGF RECEPTOR PROTEIN TYROSINE KINASE

FIELD OF THE INVENTION

This invention relates to the inhibition of cell proliferation. More specifically, this invention relates to the use of pyrazolo[3,4-g]quinoxaline compounds in inhibiting cell proliferation, including compounds which are useful protein tyrosine kinase (PTK) inhibitors.

Normal cellular reproduction is believed to be triggered by the exposure of the cellular substrate to one or more growth factors, examples of which are insulin, epidermal growth factor (EGF) and platelet-derived growth factor (PDGF). Such growth factor receptors are imbedded in and penetrate through the cellular membrane. The initiation of cellular reproduction is believed to occur when a growth factor binds to the corresponding receptor on the external surface of the cellular membrane. This growth factor-receptor binding alters the chemical characteristics of that portion of the receptor which exists within the cell and which functions as an enzyme to catalyze phosphorylation of either an intracellular substrate or the receptor itself, the latter being referred to as autophosphorylation. Examples of such phosphorylation enzymes include tyrosine kinases, which catalyze phosphorylation of tyrosine amino acid residues of substrate proteins.

Initiation of autophosphorylation, i.e., phosphorylation of the growth factor receptor itself, and of the phosphorylation of a host of intracellular substrates are some of the biochemical events which are involved in mitogenesis and cell proliferation. Phosphorylation of substrate proteins by other receptors are the earliest identifiable biochemical hormonal responses.

Compounds described in this invention can be applied to the treatment of various disease states which are characterized by uncontrolled cellular proliferation. These disease states involve a variety of cell types and include disorders such as restenosis occurring after angioplasty, atherosclerosis, leukemia, rheumatoid arthritis, transplantation atherosclerosis, glomerolonephritis or tumors/cancer. The application of compounds as selective inhibitors of the protein tyrosin kinase activity may interfere with this growth factor-mediated cellular hyperplasia resulting in a therapeutic agent for the treatment of the aforementioned disorders.

Compounds of this invention are novel as selective inhibitors of the PDGF-R protein tyrosine kinase and can be applied as potential therapeutic agents for various disease states which are characterized by uncontrolled cellular proliferation.

REPORTED DEVELOPMENTS

Protein tyrosine kinases (PTKs) are a group of enzymes which play a crucial role in the regulation of cellular proliferation. These enzymes catalyze the transfer of the γ-phosphate of ATP to specific tyrosine residues in various intracellular protein substrates as well as the ligand-induced autophosphorylaion of the transmembrane receptors. This enzymatic activity has been detected in several viral and cellular oncogene products and is associated with a variety of growth factor receptors, including platelet-derived growth factor (PDGF). The interaction of PDGF with specific cell-surface receptors stimulates the associated tyrosine kinase activity. This enzyme activity is thought to be an important initial event of signal transduction mechanisms which control cellular proliferation. The restenosis of coronary arteries after balloon angioplasty is due to the intimal hyperplasia of vascular smooth muscle cells and is the major problem that limits the long-term efficacy of this procedure. Compounds which inhibit the PDG F-receptor tyrosine kinase may be useful as potential therapeutic agents for the control of this and other hyperproliferative disorders.

International Publication Number WO92/20642 to Rhone-Poulenc Rorer International (Holdings) Inc. discloses bis mono- and bicyclic aryl and heteroaryl compounds which inhibit EGF and/or PDGF receptor tyrosine kinase.

SUMMARY OF THE INVENTION

In accordance with the present invention, compounds are provided which possess properties which are capable of inhibiting abnormal cell proliferation in a patient suffering from a disorder characterized by such proliferation. Further, the present invention provides a method for treating such disorders comprising the administration to a patient of a PDGF receptor inhibiting effective amount of a pyrazolo[3,4-g]quinoxaline compound exhibiting protein tyrosine kinase inhibition activity wherein there is further attached to the quinoxalinyl portion of the molecule an aryl or heteroaryl group. Said compounds being optionally substituted or polysubstituted.

Another aspect of the present invention relates to pharmaceutical compositions comprising, in admixture with a pharmaceutically acceptable carrier, a pharmaceutically effective amount of a novel compound of the aforementioned type. Another aspect of this invention comprises novel compounds useful in the practice of the present method.

More specifically, the compounds of this invention may be described by the compounds of Formula I:

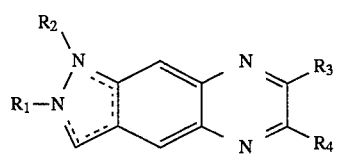

Formula I where:

------ may be a double bond;

$R_1$ or $R_2$ is hydrogen, acyl, 1,2-dihydroxyethyl, 1,2-dihydroxyprop-3-yl, or $$\begin{array}{c} R_5 \\ | \\ (CR)_x - X; \end{array}$$

$R_3$ or $R_4$ is Y—Ar the other being hydrogen;

$R_5$ is hydrogen, alkyl, hydroxy, alkoxy, carboxy, carbalkoxy or carbamoyl;

R is hydrogen or alkyl

X is hydrogen, $C_4$–$C_6$ alkyl, alkenyl, hydroxy, alkoxy, carboxy, carbalkoxy, acyl, acyloxy, amino, mono- or di-alkyl-amino, acylamino, cyano, carbamoyl, acylcarbamoyl, mono- or di-alkylcarbamoyl, thiocarbamoyl, mono- or dialkylthiocarbamoyl, acylthio-carbamoyl, 2,2-dialkyl-1,3-dioxolan-5-yl, 5-tetrazolyl, piperdinyl, pyridyl, phenyl or substituted phenyl where the substitution may be one or two groups independently selected from alkyl, alkoxy, carboxy, carbalkoxy, carbamoyl, mono- or di-alkylcarbamoyl, thiocarbamoyl, mono- or dialkylthiocarbamoyl, halo or haloalkyl;

Y is a bond, $(CH_2)_{1-3}$, $(CH_2)_nO(CH_2)_m$, $(CH_2)_nS(CH_2)_m$, or $(CH_2)_nNR(CH_2)_m$;

n and m are independently 0–3 and n+m=0–3;

x is 1–3;

Ar is phenyl, substituted phenyl, thienyl, substituted thienyl, pyridyl, substituted pyridyl, α or β naphthyl or substituted α or β naphthyl where the substitution may be one or two groups independently selected from alkyl, hydroxy, alkoxy, halo, haloalkyl or cyano; or a pharmaceutically acceptable salt thereof.

DETAILED DESCRIPTION AND PREFERRED EMBODIMENTS

The pyrazolo[3,4-g]quinoxaline nomenclature used in this invention is as follows:

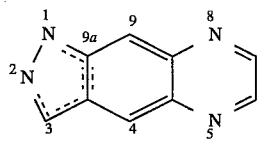

As employed above and throughout this disclosure, the following terms, unless otherwise indicated, shall be understood to have the following meanings:

"Alkyl" means a saturated aliphatic hydrocarbon, either branched- or straight-chained. Preferred alkyl is "loweralkyl" having about 1 to about 6 carbon atoms. Examples of alkyl include methyl, ethyl, n-propyl, isopropyl, butyl, sec-butyl, t-butyl, pentyl and hexyl.

"Alkenyl" refers to an unsaturated or partially unsaturated hydrocarbon group containing from 2 to about 7 carbon atoms which may be straight chained or branched. Allyl is preferred.

"Alkoxy" refers to an alkyl-O-group. Preferred alkoxy groups are

"loweralkoxy" having about 1 to about 6 carbon atoms. Examples include methoxy, ethoxy, propoxy, i-propoxy, butoxy and t-butoxy.

"Acyl" refers to any organic radical derived from an organic acid by the removal of its hydroxy group such as formyl, acetyl, propionyl, i-propionyl, butyryl and t-butyryl.

"Acylamino" ferers to an amino group substituted by an acyl radical.

"Acyloxy" refers to an acyl-O-group. Preferred acyloxy groups include acetyloxy, propionyloxy, i-propionyloxy, butyryloxy and t-butyryloxy "Carboxy" means —COOH.

"Carbalkoxy" means an alkyl ester of a carboxylic acid.

"Carbamoyl" refers to any organic radical derived from an organic acid by removal of its hydroxy group and replacing it with an amine or substituted amine. Preferred carbamoyl groups include carbamoyl, mono- and di-alkylcarbamoyl and acylcarbamoyl.

"Thiocarbamoyl" means a carbamoyl where the oxygen has been replaced with sulfur. Preferred thiocarbamoyl groups include thiocarbamoyl, mono- and di-alkylthiocarbamoyl and acylthiocarbamoyl "Halo" means halogen. Preferred halogens include chloride, bromide and fluoride.

The preferred haloalkyl group is trifluoromethyl.

The more preferred compounds of this invention include those compounds of Formulae II–V.

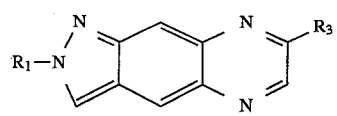

Formula II

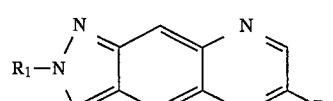

Formula III

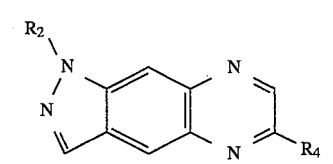

Formula IV

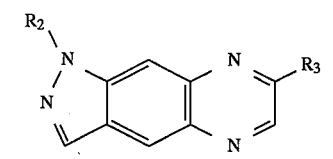

Formula V

Still more preferred compounds are described by Formulae II–V where:

R is hydrogen or loweralkyl;

X is hydrogen, hydroxy, loweralkoxy, carboxy, carbloweralkoxy, phenyl or substituted phenyl where the substitution may be one or two groups independently selected from loweralkyl, loweralkoxy, carboxy, carblower-alkoxy, carbamoyl, chloro, fluoro or trifluoromethyl;

Y is a bond, $(CH_2)_{1-3}$ or $O(CH_2)_{1-3}$;

Ar is phenyl, substituted phenyl, thienyl or substituted thienyl where the substitution may be one or two groups independently selected from loweralkyl, hydroxy, loweralkoxy, chloro, fluoro or trifluoromethyl. chloro, fluoro or trifluoromethyl.

The most preferred compounds are described by Formulae VI–XIII.

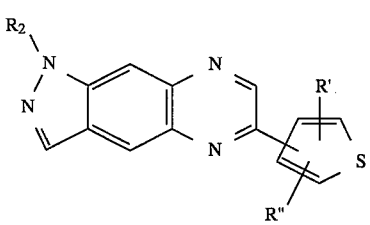

Formula VI

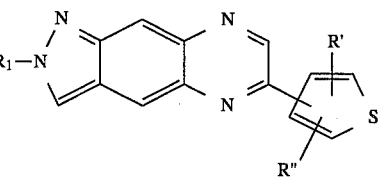

Formula VII

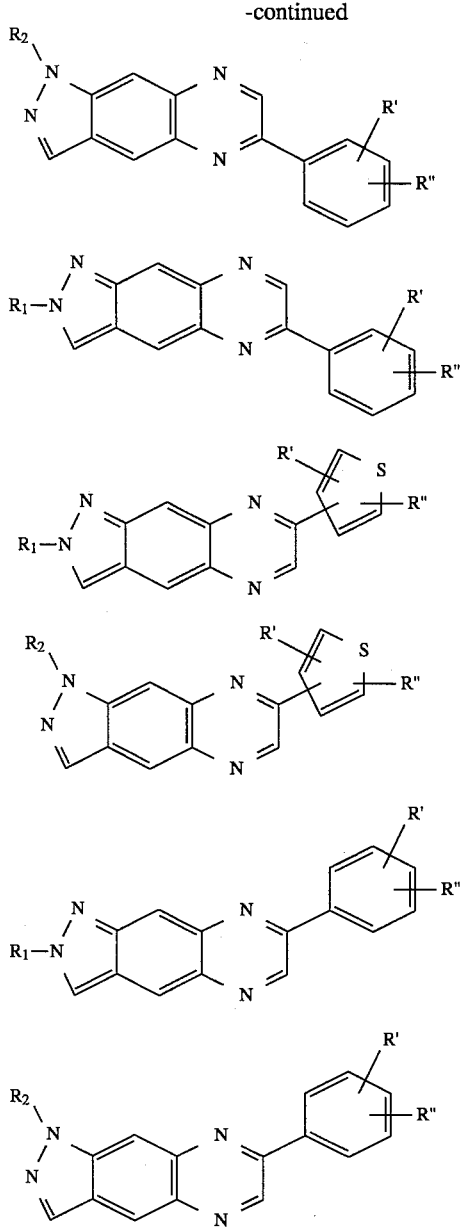

where:

R₁ or R₂ is hydrogen, acyl, 1,2-dihydroxyethyl, 1,2-dihydroxyprop-3-yl, or

R is hydrogen or loweralkyl;

X is hydrogen, hydroxy, loweralkoxy, carboxy, carbloweralkoxy, phenyl or substituted phenyl where the substitution may be one or two groups independently selected from alkyl, alkoxy, carboxy or carbloweralkoxy and carbamoyl;

x is 1–3;

R' and R" are independently selected from loweralkyl, hydroxy, loweralkoxy, halo or trifluoromethyl;

Representative compounds include the following:

7-(5-chlorothien-2-yl)-1H-pyrazolo[3,4-g]quinoxaline 1-methyl-7-(5-chlorothien-2-yl)-1H-pyrazolo[3,4-g]quinoxaline 2-methyl-7-(5-chlorothien-2-yl)-2H-pyrazolo[3,4-g]quinoxaline 7-(3-fluoro-4-methoxyphenyl)-1H-pyrazolo[3,4-g]quinoxaline 1-methyl-7-(3-fluoro-4-methoxyphenyl)-1H-pyrazolo[3,4-g]quinoxaline 2-methyl-7-(3-fluoro-4-methoxyphenyl)-2H-pyrazolo[3,4-g]quinoxaline 1-acetyl-7-(3-fluoro-4-methoxyphenyl)-1H-pyrazolo[3,4-g]quinoxaline 2-acetyl-7-(3-fluoro-4-methoxyphenyl)-2H-pyrazolo[3,4-g]quinoxaline 1-allyl-7-(3-fluoro-4-methoxyphenyl)-1H-pyrazolo[3,4-g]quinoxaline 2-allyl-7-(3-fluoro-4-methoxyphenyl)-2H-pyrazolo[3,4-g]quinoxaline 1-ethyl-7-(3-fluoro-4-methoxyphenyl)-1H-pyrazolo[3,4-g]quinoxaline 2-ethyl-7-(3-fluoro-4-methoxyphenyl)-2H-pyrazolo[3,4-g]quinoxaline 1-benzyl-7-(3-fluoro-4-methoxyphenyl)-1H-pyrazolo[3,4-g]quinoxaline 2-benzyl-7-(3-fluoro-4-methoxyphenyl)-2H-pyrazolo[3,4-g]quinoxaline 2-(2-t-butyryloxymethyl)-7-(3-fluoro-4-methoxyphenyl)-2H-pyrazolo[3,4-g]quinoxaline 1-(2-t-butyryloxymethyl)-7-(3-fluoro-4-methoxyphenyl)-1H-pyrazolo[3,4-g]quinoxaline 2-(2-t-butyryloxymethyl)-6-(3-fluoro-4-methoxyphenyl)-2H-pyrazolo[3,4-g]quinoxaline 1-(2-t-butyryloxymethyl)-6-(3-fluoro-4-methoxyphenyl)-1H-pyrazolo[3,4-g]quinoxaline 1-carboethoxymethyl-7-(3-fluoro-4-methoxyphenyl)-1H-pyrazolo[3,4-g]quinoxaline 2-carboethoxymethyl-7-(3-fluoro-4-methoxyphenyl)-2H-pyrazolo[3,4-g]quinoxaline 6-(3-fluoro-4-methoxyphenyl)-1H-pyrazolo[3,4-g]quinoxaline 1-(2-acetoxyethyl)-7-(3-fluoro-4-methoxyphenyl)-1H-pyrazolo[3,4-g]quinoxaline 2-(2-acetoxyethyl)-[7-(3-fluoro-4-methoxyphenyl)-2H-pyrazolo[3,4-g]quinoxaline 1-carboxymethyl-7-(3-fluoro-4-methoxyphenyl)-1H-pyrazolo[3,4-g]quinoxaline 2-carboxymethyl-7-(3-fluoro-4-methoxyphenyl)-2H-pyrazolo[3,4-g]quinoxaline 1-cyanomethyl-7-(3-fluoro-4-methoxyphenyl)-1H-pyrazolo[3,4-g]quinoxaline 2-cyanomethyl-7-(3-fluoro-4-methoxyphenyl)-2H-pyrazolo[3,4-g]quinoxaline 1-[2-hydroxyethyl]-7-(3-fluoro-4-methoxyphenyl)-1H-pyrazolo[3,4-g]quinoxaline 2-[2-hydroxyethyl]-7-(3-fluoro-4-methoxyphenyl)-2H-pyrazolo[3,4-g]quinoxalin 2-[2-hydroxyethyl]-6-(3-fluoro-4-methoxyphenyl)-2H-pyrazolo[3,4-g]quinoxaline 1-(N-piperdinylethyl)-7-(3-fluoro-4-methoxyphenyl)-1H-pyrazolo[3,4-g]quinoxaline 2-(N-piperdinylethyl)-7-(3-fluoro-4-methoxyphenyl)-2H-pyrazolo[3,4-g]quinoxaline 1-[(4R)-2,2-dimethyl-[1,3]dioxolan-4-ylmethyl]-7-(3-fluoro-4-methoxyphenyl)-1 H-pyrazolo[3,4-g]quinoxaline 2-[(4R)-2,2-dimethyl-[1,3]dioxolan-4-ylmethyl]-7-(3-fluoro-4-methoxyphenyl)-2 H-pyraazolo[3,4-g]quinoxaline 1[(2R)-1,2-dihydroxyprop-3-yl)-7-(3-fluoro-4-methoxyphenyl)-1H-pyrazolo-[3,4-g]-quinoxaline
2-[(2R)-1,2-dihydroxyprop-3-yl)-7-(3-fluoro-4-methoxyphenyl)-2H-pyrazolo-[3,4-g]-quinoxaline
7-(3-fluorophenyl)-1H-pyrazolo[3,4-g]quinoxaline
7-(thien-3-y)l-1H-pyrazolo[3,4-g]quinoxaline
1-methyl-7-(thien-3-yl)-1H-pyrazolo[3,4-g]quinoxaline
2-methyl-7-(thien-3-yl)-2H-pyrazolo[3,4-g]quinoxaline
7-phenethyl-1H-pyrazolo[3,4-g]quinoxaline
6-(thien-3-yl)-1H-pyrazolo[3,4-g]quinoxaline
1-(2-methoxyethyl)-7-(thien-3-yl)-1H-pyrazolo[3,4-g]quinoxaline
2-(2-methoxyethyl)-7-(thien-3-yl)-2H-pyrazolo[3,4-g]quinoxaline 1-acetamido-7-(thien-3-yl)-1H-pyrazolo[3,4-g]quinoxaline
2-acetamido-7-(thien-3-yl)-2H-pyrazolo[3,4-g]quinoxaline
1-(pyrid-3-ylmethyl)-7-(3-fluoro-4-methoxyphenyl)-1H-pyrazolo[3,4-g]quinoxaline
2-(pyrid-3-ylmethyl)-7-(3-fluoro-4-methoxyphenyl)-2H-pyrazolo[3,4-g]quinoxaline
1-(pyrid-2-ylmethyl)-7-(3-fluorophenyl)-1H-pyrazolo[3,4-g]quinoxaline
2-(pyrid-2-ylmethyl)-7-(3-fluorophenyl)-2H-pyrazolo[3,4-g]quinoxaline
1-hydroxyethyl-7-(thien-3-yl)-1H-pyrazolo[3,4-g]quinoxaline
2-hydroxyethyl-7-(thien-3-yl)-2H-pyrazolo[3,4-g]quinoxaline
1-(2-N,N-diethylacetamido)-7-(3-fluoro-4-methoxyphenyl)-1H-pyrazolo[3,4-g]quinoxaline
2-(2-N,N-diethylacetamido)-7-(3-fluoro-4-methoxyphenyl)-2H-pyrazolo[3,4-g]quinoxaline
1-(3-thioproionamido)-7-(3-fluorophenyl)-1H-pyrazolo[3,4-g]quinoxaline
2-(3-thioproionamido)-7-(3-fluorophenyl)-2H-pyrazolo[3,4-g]quinoxaline
1-(3-carboxyethyl)-7-(3-fluorophenyl)-1H-pyrazolo[3,4-g]quinoxaline
2-(3-carboxyethyl)-7-(3-fluorophenyl)-2H-pyrazolo[3,4-g]quinoxaline
1-(2-N,N-dimethylaminoethyl)-7-(3-fluoro-4-methoxyphenyl)-1H-pyrazolo[3,4-g]quinoxaline
2-(2-N,N-dimethylaminoethyl)-7-(3-fluoro-4-methoxyphenyl)-2H-pyrazolo[3,4-g]quinoxaline The compounds of this invention may be prepared by the following general reaction schemes.

STEP A

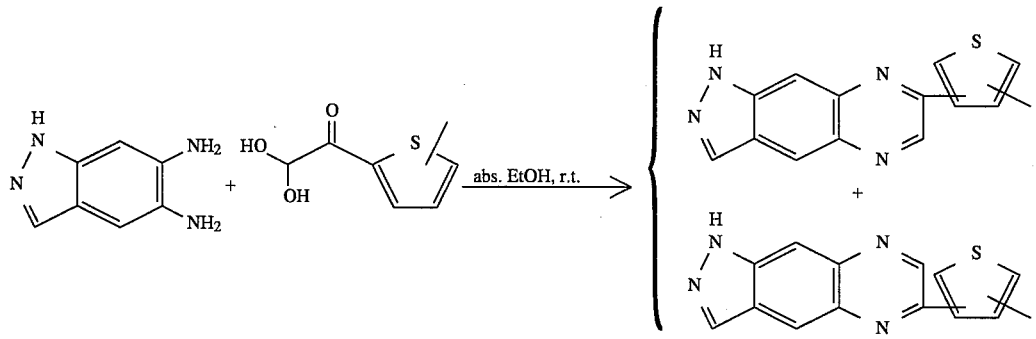

STEP Ba

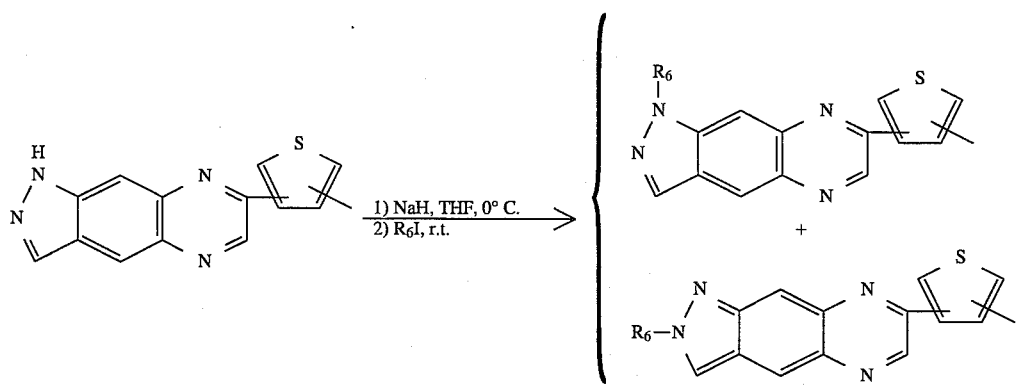

STEP Bb
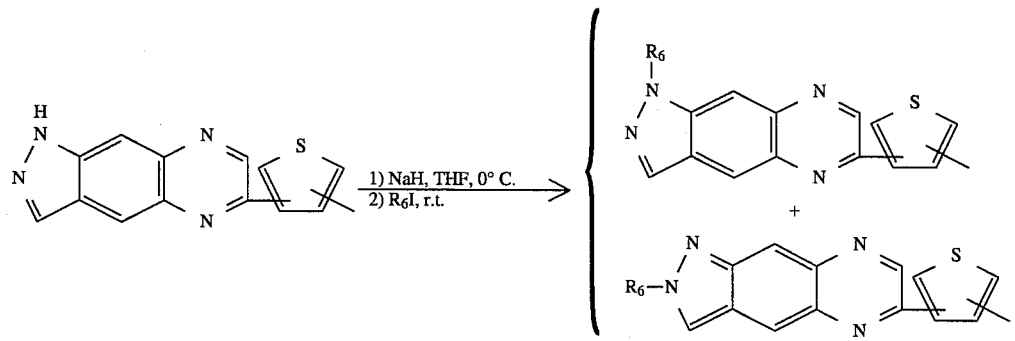
STEP C
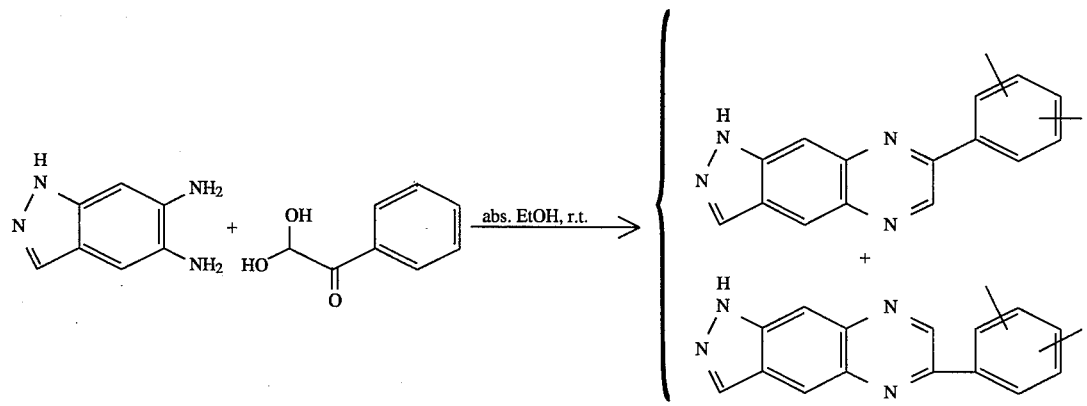
STEP Da
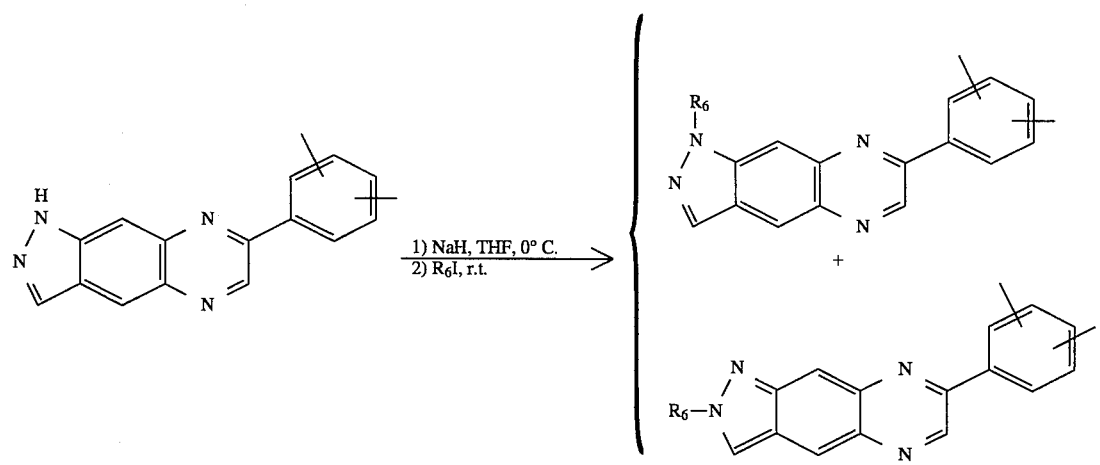

-continued
STEP Db
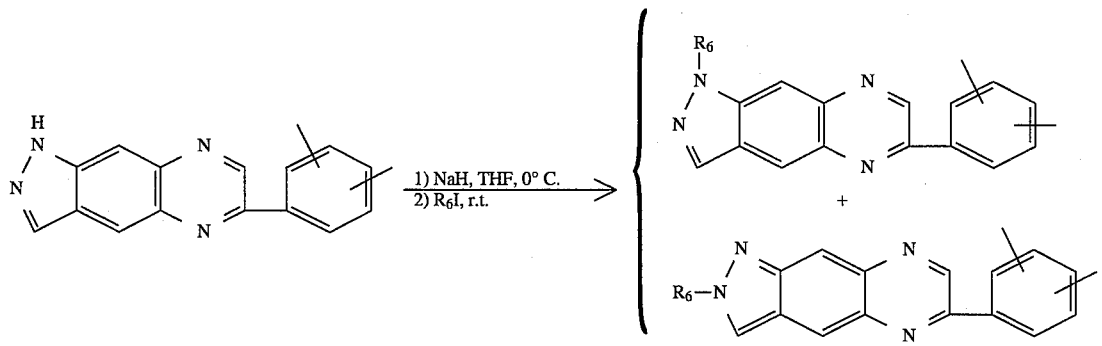
STEP Ea
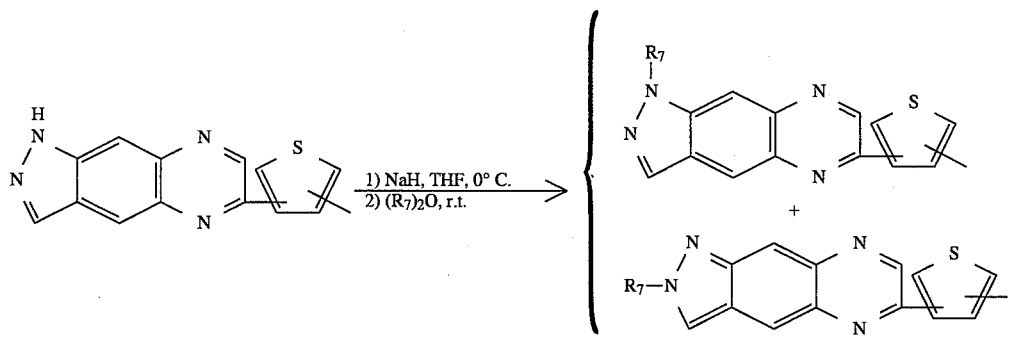
STEP Eb
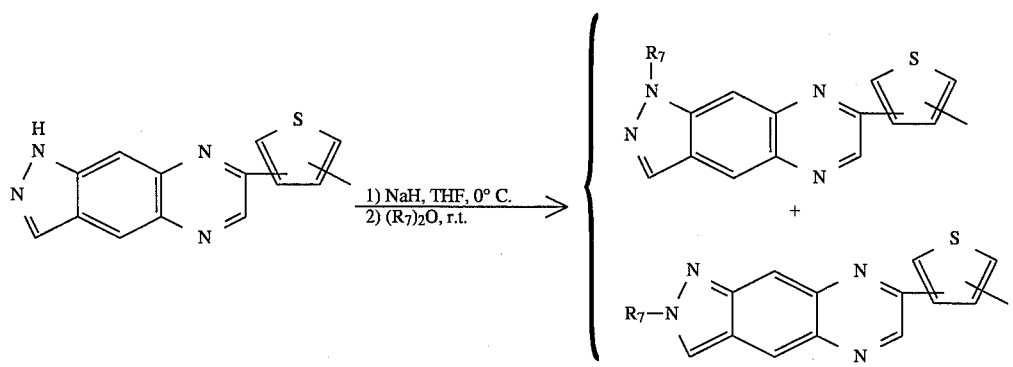

STEP Fa

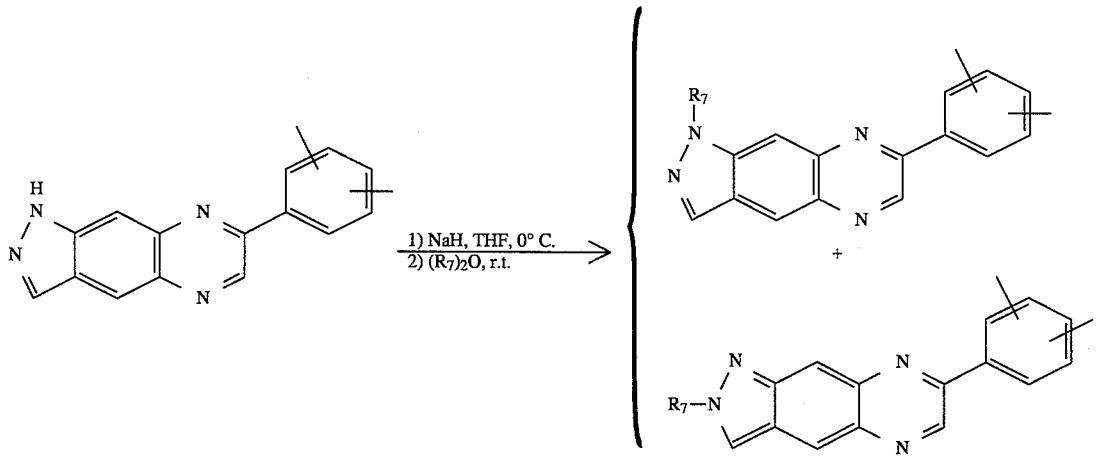

STEP Fb

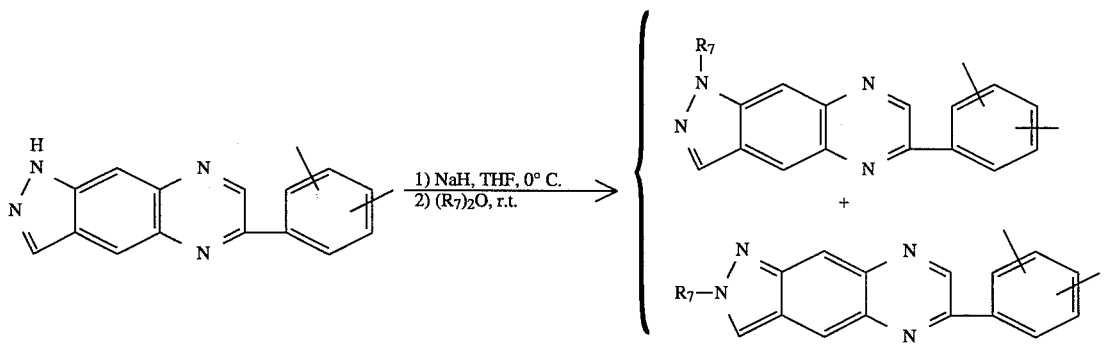

where:

R₆ is defined as R₁ and R₂ and is other than hydrogen and acyl and

R₇ is acyl.

Condensation as shown in Step A of 5,6-diaminoindazole with a glyoxyloylthiophene in the presence of absolute alcohol results in ring formation of a mixture of 6-thienyl-1H-pyrazolo[3,4-g]quinoxaline and 7-thienyl-1H-pyrazolo [3,4-g]quinoxaline. These positional isomers can be separated by standard procedures, such as column chromatography.

A similar preparation as shown in Step C may be carried out to obtain 6-substituted phenyl-1H-pyrazolo[3,4-g]quinoxaline and 7-substituted phenyl-1H-pyrazolo[3,4-g]quinoxaline.

When the 6-thienyl or 7-thienyl-1H-pyrazolo[3,4-g]quinoxalines as shown in Steps Ba and Ab are reacted with sodium hydride in a polar medium, as as THF at reduced temperatures, followed by treatment with a substituted alkyl halide at room temperature results in a mixture of the 1-substituted-6-thienyl or 7-thienyl-1H-pyrazolo[3,4-g]quinoxaline and 2-substituted-6-thienyl or 7-thienyl-2H-pyrazolo[ 3,4-g]quinoxaline. If desired an alkyl rosylate or mesylate may be employed in place of the alkyl halide.

These positional isomers may also be separated by standard procedures, such as column chromatography.

A similar preparation as shown in Steps Da and Db may be carried out to obtain 1-substituted-6-substituted phenyl or 7-substituted phenyl-1H-pyrazolo[3,4-g]quinoxaline and 2-substituted-6-substituted phenyl or 7-substituted phenyl-2H-pyrazolo[3,4-g]quinoxaline.

When it is desired to have a substituent at the 1- or 2-position as which consists of an aryl group as shown insteps Ea and Eb then the 6-thienyl or 7-thienyl-1H-pyrazolo[ 3,4-g]quinoxaline are reacted, as above, with sodium hydride in a polar medium, such as THF at reduced temperature, followed by treatment with the appropriate anhydride at room temperature gives 1-substituted-6-thienyl or 7-thienyl-1H-pyrazolo[3,4-g]quinoxaline and 2-substituted-6-thienyl or 7-thienyl-2H-pyrazolo[3,4-g]quinoxaline. These positional isomers may be separated by standard procedures, such as column chromatography.

A similar preparation as shown in Steps Fa and Fb may be carried out to obtain 1-substituted-6-phenyl or 7-phenyl-1H-pyrazolo[3,4-g]quinoxaline and 2 -substituted-6-phenyl or 7-phenyl-2H-pyrazolo[3,4-g]quinoxaline.

The starting materials of this invention are either known or can be prepared by known methods using readily available materials. Thus for example a substituted acetylthiophene when treated with selenium oxide in an aqueous dioxane media at raised temperatures results in the corresponding substituted glyoxyloylthiophene. Likewise the substituted glyoxyloylbenzenes may be prepared.

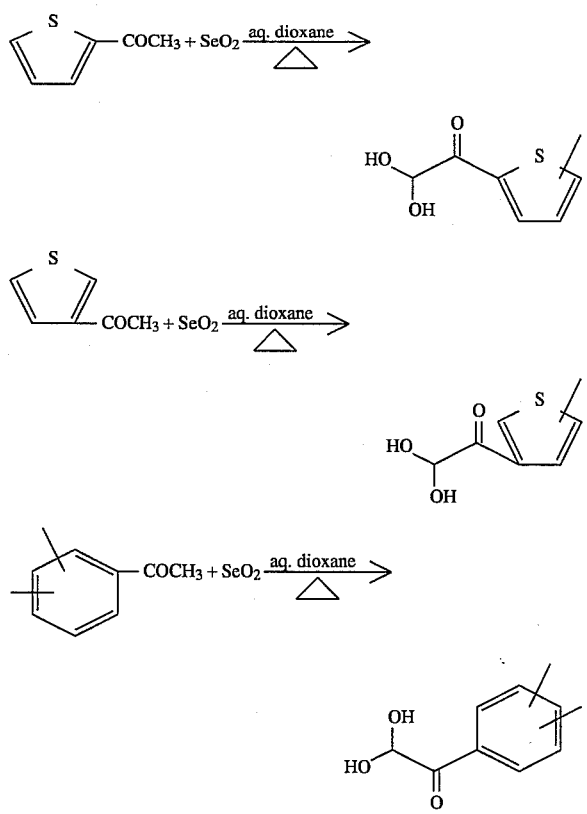

The compounds of this invention may be useful in the form of the free base, in the form of salts and as a hydrate. All forms are within the scope of this invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Certain compounds of this invention may have at least one asymmetric carbon atom. As a result, those compounds of this invention may be obtained either as racemic mixtures, diastereoisomeric mixtures or as individual enantiomers. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds*: Optical Resolution Information Center, Manhattan College, Riverdale, N.Y. Such procedures are useful in the practice of this invention. A further useful reference is *Enantiomers, Racemates and Resolutions*: Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

Various substituents on the present new compounds can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "*Protective Groups in Organic Synthesis*" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids. Thus, substitution or alteration reactions can be employed to provide a variety of substituents throughout the molecule of the starting material, intermediates, or the final product.

The compounds of this invention may be prepared by employing procedures known in the literature starting from known compounds or readily preparable intermediates.

Exemplary general procedures follow.

The compounds of the present invention may be prepared by the following representative examples.

EXAMPLE 1

6-(5-chlorothien,2-yl)-1H-pyrazolo]3,4-g]quinoxaline
7-(5-chlorothien-2-yl)-1H-pyrazolo[3,4-g]quinoxaline STEP A 2-chloro-5-glyoxyloylthiophene Selenium oxide (6.88%) is heated to dissolve in 100 ml aqueous dioxane (95:5 dioxane: $H_2O$). The 2-acetyl-5-chlorothiophene (5.00 g) is added to the mixture. The resulting mixture is refluxed overnight, then cooled. The precipitated selenium metal is filtered after solvent removal a brown thick oil results which solidifies on standing. The solid is heated to dissolve in 400 ml hot water, filtered and allowed to cool to room temperature. The precipitate is collected by filtration, washed with fresh $H_2O$ and dried to obtain a light brown flake. The second crop is obtained by extracting the mother liquid with ethylacetate, separated, dried ($MgSO_4$) and concentrated in vacuo to give a light yellow solid which upon treatment with HPLC gives 2-chloro-5-glyoxyloylthiophene, which is used directly in the next step.

STEP B 6-(5-chlorothien-2-yl)-1H-pyrazolo[3,4-g]quinoxaline 7-(5-chlorothien-2-yl)-1H-pyrazolo[3,4-g]quinoxaline To a mixture of 5,6-diaminoindazole (0.5 g) in 30 ml absolute ethanol is added slowly a solution of 2-chloro-5-glyoxyloylthiophene (0.72 g) and 20 ml ethanol. The resulting mixture is stirred at room temperature for 4.5 hours. The yellow solid which forms is filtered off, washed with ethanol then with hexane and air dried overnight.

The products are separated and purified by silica gel column chromatography using 3%, 6% then 9% of ethylacetate in methylene chloride as eluent to obtain 6-(5-chlorothien-2-yl)-1H-pyrazolo[3,4-g]quinoxaline and 7-(5-chlorothien-2-yl)-1H-pyrazolo[3,4-g]quinoxaline (m.p. >300° C.).

EXAMPLE 2

6-(thien-3-yl)-1H-pyrazolo[3,4-g]quinoxaline
7-(thien-3-yl)-1H-pyrazololo[3,4-g]quinoxaline When the procedure of Example 1 is followed and 2-acetyl-5-chlorothiophene is replaced with 3-acetylthiophene, then the products prepared are 6-(thien-2-yl)-1H-pyrazolo[3,4-g]quinoxaline and 7-(thien-2-yl)-1H-pyrazolo[3,4-g]quinoxaline.

EXAMPLE 3

6-(3-fluoro-4-methoxyphenyl)-1H-pyrazolo[3,4-g]quinoxaline
7-(3-fluoro-4-methoxyphenyl)-1H-pyrazolo[3,4-g]quinoxaline STEP A 1-methoxy-2-fluoro-4-glyoxyloylbenzene Selenium oxide (4.953 g) is heated to dissolve in 100 ml aqueous dioxane (95:5 dioxane: $H_2O$). The 3-fluoro-4-methoxyacetophenone (5.00 g) is added to the mixture. The resulting mixture is refluxed overnight then coiled. The precipitated selenium metal is filtered. The filtrate is concentrated in vacuo to give a brown thick gum. It is recrystallized from ~200 ml hot $H_2O$, filtered hot and allowed to stand at RT overnight. The precipitated pale pink flake are filtered, washed with $H_2O$ and let air dried to give 1-methoxy-2-fluoro-4-glyoxyloylbenzene, which is used directly in the next step.

STEP B 6-(3-fluoro-4-methoxyphenyl)-1H-pyrazolo[3,4-g]quinoxaline 7-(3-fluoro-4-methoxyphenyl)-1H-pyrazolo[3, 4-g]quinoxaline To an ice-cooled mixture of 5,6-diaminoindazole (0.5 g) in 20 ml absolute ethanol is added slowly a solution of 1-methoxy-2-fluoro-4-glyoxyloylbenzene (0.75 g) in 30 ml ethanol. The resulting mixture is stirred at room temperature over night. The solid which forms is filtered off, washed with a small amount of ethanol then with hexane and air dried to give a yellow material.

The products are separated and purified by silica gel column chromatography using 3%, 6% then 9% of ethylacetate in methylene chloride as eluent to obtain 7-(3-fluoro-4-methoxyphenyl)-1H-pyrazolo[3,4-g]quinoxaline (m.p. 283°–285° C.) and then with 20%, 30% and 40% of ethylacetate in methylene chloride as eluent to obtain 6-(3-fluoro-4-methoxyphenyl)-1H-pyrazolo[3,4-g]quinoxaline (m.p.>250° C.).

EXAMPLE 4

1-methyl-7-(5-chlorothien-2-yl)-1H-pyrazolo[3,4-g]quinoxaline 2-methyl-7-(5-chlorothien-2-yl)-2H-pyrazolo[3,4-g]quinoxaline To an ice-colded suspension of NaH (0.062 g) in 20 ml of anhydrous THF under $N_2$ is added 7-(5-chlorothien-2-yl)-1H-pyrazolo[3,4-g]quinoxaline (0.63 g). The orange-red mixture is stirred at the same temperature for 5 minutes, then iodomethane (0.374 g) is added dropwise to the orange-red mixture. The resulting mixture is stirred at room temperature overnight, then poured into water, extracted with methylene chloride, separated, dried ($MeSO_4$), concentrated in vacuo to give a yellow solid. Purification is by chromatography eluting first with 5% ethylacetate in hexane, then gradually up to 30% ethylacetate in hexane to isolate 1-methyl-7-(5-chlorothien-2-yl)-1H-pyrazolo[3,4-g]quinoxaline (m.p. 225°–227° C.), then up to 10% hexane in ethylacetate to isolate 2-methyl-7-(5-chlorothien-2-yl)-2H-pyrazolo[3,4-g]quinoxaline (m.p. 222°–224° C.).

EXAMPLE 5

1-methyl-7-(3-fluoro-4-methoxyphenyl)-1H-pyrazolo[3,4-g]quinoxaline 2-methyl-7-(3-fluoro-4-methoxyphenyl)-2H-pyrazolo[3,4-g]quinoxaline When the procedure of Example 4 is followed and 7-(5-chlorothien-2-yl)-H-pyrazolo[3,4-g]quinoxaline is replaced with 7-(3-fluoro-4-methoxyphenyl)-1H-pyrazolo[3,4-g]quinoxaline, then the products prepared are 1-methyl-7-(3-fluoro-4-methoxyphenyl)-1H-pyrazolo[3,4-g]quinoxaline (m.p. 229°–231° C.) and 2-methyl-7-(3-fluoro-4-methoxyphenyl)-2 H-pyrazolo[3,4-g]quinoxaline (m.p. 201°–205° C.).

EXAMPLE 6

1-ethyl-7-(3-fluoro-4-methoxyphenyl)-1H-pyrazolo[3,4-g]quinoxaline 2-ethyl-7-(3-fluoro-4-methoxyphenyl)-2H-pyrazolo[3,4-g]quinoxaline When the procedure of Example 4 is followed and iodomethane is replaced with iodoethane, then the products prepared are 1-ethyl-7-(3-fluoro-4-methoxyphenyl)-1H-pyrazolo[ 3,4-g]quinoxaline (m.p. 164°–171° C.) and 2-ethyl-7-(3-fluoro-4-methoxyphenyl)-2H-pyrazolo[3,4-g]quinoxaline (m.p. 185°–189° C.).

EXAMPLE 7

1-acetyl-7-(3-fluoro-4-methoxyphenyl)-1H-pyrazolo[3,4-g]quinoxaline 2-acetyl-7-(3-fluoro-4-methoxyphenyl)-2H-pyrazolo[3,4-g]quinoxaline To an ice-colded suspension of NaH (0.029 g) in 30 ml of anhydrous THF under $N_2$ is added 7-(3-fluoro-4-methoxyphenyl)-1H-pyrazolo[3,4-g]quinoxaline (0.30 g). The orange-red mixture is stirred at the same temperature for 5 minutes, then acetic anhydride (0.122 g) is added dropwise to the mixture. A yellow solid forms during the acetic anhydride additions. The resulting mixture is stirred at room temperature overnight. The mixture is poured into water. The yellow solid is filtered, washed with water then with ether and dried. The product is purified by column chromatography eluting with 15% ethylacetate in hexane, 25% ethylacetate in hexane then 5% ethylacetate in methylene chloride to obtain 1-acetyl-7-(3-fluoro-4-methoxyphenyl)-1H-pyrazolo[3,4-g]quinoxaline (m.p. 261°–265° C.) and 1-acetyl-7-(3-fluoro-4-methoxyphenyl)-2H-pyrazolo[3,4-g]quinoxaline.

EXAMPLE 8

1-allyl-7-(3-fluoro-4-methoxyphenyl)-1H-pyrazolo[3,4-g]quinoxaline 2-allyl-7-(3-fluoro-4-methoxyphenyl)-2H-pyrazolo[3,4-g]quinoxaline To a suspension of 0.50 g of 7-(3-fluoro-4-methoxyphenyl)-1H-pyrazolo[3,4-g]quinoxaline, 30 ml of anhydrous THF is added 0.061 g of 60% NaH. It is stirred at room temperature for 10 minutes, then allyl bromide 0.206 g is added dropwise into the red mixture. The resulting mixture is stirred at room temperature overnight then poured into water, extracted with methylene chloride and the organic layer is separated, dried ($Na_2SO_4$), concentrated in vacuo which gives yellow crude product. This is purified by silica-gel column chromatography using methylene chloride, then changed to 1%–4% acetone/methylene chloride as the solvent system to obtain 1-allyl-7-(3-fluoro-4-methoxyphenyl)-1H-pyrazolo[3,4-g]quinoxaline (m.p. 121°–124° C.) and 2-allyl-7-(3-fluoro-4-methoxy-phenyl)-2H-pyrazolo[3,4-g]quinoxaline (m.p. 196°–200° C.).

EXAMPLE 9

1-benzyl-7-(3-fluoro-4-methoxyphenyl)-1H-pyrazolo[3,4-g]quinoxaline 2-benzyl-7-(3-fluoro-4-methoxyphenyl)-2H-pyrazolo[3,4-g]quinoxaline To a suspension of 0.50 g of 7-(3-fluoro-4-methoxyphenyl)-1H-pyrazolo[3,4-g]quinoxaline, 30 ml of anhydrous THF is added 0.061 g of 60% NaH. The red-orange mixture is stirred at room temperature for 10 minutes, then 0.265 g of benzyl iodide is added and is stirred at room temperature overnight. The mixture is filtered, washed with $CH_2Cl_2$. The filtrate and the $CH_2Cl_2$ wash are combined and mixed with water, extracted with $CH_2Cl_2$, separated, dried ($Na_2SO_4$) and concentrated in vacuo to give yellow crude solid. This is purified by silica-gel column chromatography using the combination of ethylacetate: hexane: methylene chloride as solvent to obtain 1-benzyl-7-(3-fluoro-4-methoxyphenyl)-1H-pyrazolo[3,4-g]quinoxaline (m.p. 149°–155° C.) and 2-benzyl-7-(3-fluoro-4-methoxyphenyl)-2H-pyrazolo[3,4-g]quinoxaline (m.p. 225°–227° C.).

EXAMPLE 10

1-(2-t-butyryl)-6-(3-fluoro-4-methoxyphenyl)-2H-pyrazolo[3,4-g]-quinoxaline 2-(2-t-butyryloxymethyl)-6-(3-fluoro-4-methoxyphenyl)-1H-pyrazolo[3,4-g]-quinoxaline NaH (60%, 1.84 g) is added slowly into a mixture of 15.04 g of 6-(3-fluoro-4-methoxyphenyl)-1H-pyrazolo[3,4-g]quinoxaline in 150 ml of anhydrous THF. This is stirred at room temperature for 15 minutes, then 7.7 g of 2-t-butyryloxymethyl iodide is added dropwise into the mixture slowly. The mixture is then stirred at room temperature. The mixture is filtered and the filtrate washed with water, extracted with methylene chloride, separated, dried ($Na_2SO_4$) and concentrated in vacuo to give 13.46 g of crude yellow solid, which is purified by silica-gel column chromatography using ethylacetate:methylene chloride:hexane as eluent starting from the combination ratio of 1:3:6, respectively, and changed the methylene chloride and hexane ratio with ethylacetate cause (e.g., 1:3.5:5.5; 1:4:5→1:6:3) to obtain 2-(2-t-butyryloxymethyl)-6 -(3-fluoro-4-methoxyphenyl)-1H-pyrazolo[3,4-g]-quinoxaline (m.p. 199°–201° C.).

EXAMPLE 10

1-(2-t-butyryl)-7-(3-fluoro-4-methoxyphenyl)-2H-pyrazolo[3,4-g]-quinoxaline 2-(2-t-butyryloxymethyl)-7-(3-fluoro-4-methoxyphenyl)-1H-pyrazolo[3,4-g]-quinoxaline When the procedure of Example 10 is followed and 6-(3-fluoro-4-methoxyphenyl)-1H-pyrazolo[3,4-g]quinoxaline is replaced with 7-(3-fluoro-4-methoxyphenyl)-1H-pyrazolo[3,4-g]quinoxaline, then the products prepared are 1-(2-t-butyryl)-7-(3-fluoro-4-methoxyphenyl)-2H-pyrazolo[3,4-g]-quinoxaline (m.p. 193°–194° C.) and 2-(2-t-butyryloxymethyl)-7-(3-fluoro-4 -methoxyphenyl)-1H-pyrazo[3,4-g]-quinoxaline (m.p. 161°–163° C.).

EXAMPLE 12

1-(2-acetoxyethyl)-7-(3-fluoro-4-methoxyphenyl)-1H-pyrazolo[3,4-g]quinoxaline 2-(2-acetoxyethyl-[7-(3-fluoro-4-methoxy-phenyl)-2H-pyrazolo3,4-g]quinoxaline NaH (60%; 0.35 g) is added into a stirring solution of 2.14 g of 7-(3-fluoro-4 -methoxyphenyl)-1H-pyrazolo[3,4-g]quinoxaline in 30 ml of anhydrous DMF and stirred for 15 minutes, then 1.34 g of 2-bromoethylacetate is added into the mixture slowly. The resulting mixture is stirred at room temperature for 2½ hours then poured into water and the product is filtered off, washed with water and dried. This is purified by column chromatography using 5% →20% ethylacetate in methylene chloride as eluent to obtain 1-(2-acetoxyethyl)-7-(3-fluoro-4 -methoxyphenyl)-1H-pyrazolo[3,4-g]quinoxaline (m.p. 164°–166° C.) and 2 -(2-acetoxyethyl)-7-(3-fluoro-4-methoxyphenyl)-2H-pyrazolo[3,4-g]quinoxaline (m.p. 175°–178° C.).

When 6-(3-fluoro-4-methoxyphenyl)-1H-pyrazolo[3,4-g] quinoxaline is used in the above procedure the products prepared as 1-(2-acetoxyethyl)-6-(3-fluoro-4 -methoxyphenyl)-1H-pyrazolo[3,4-g]quinoxaline and 2-(2-acetoxyethyl)-6-(3-fluoro-4-methoxyphenyl)-2H-pyrazolo[3,4-g] quinoxaline.

EXAMPLE 13

1-carboethoxymethyl-7-(3-fluoro-4-methoxyphenyl)-
1H-pyrazolo[3,4-g]quinoxaline 2-carboethoxymethyl-7-(3-fluoro-4-methoxyphenyl)-
2H-pyrazolo[3,4-g]quinoxaline When the procedure of Example 12 is followed and acetoxyethylbromide is replaced by ethylbromoacetate, then the product is prepared is 1-carboethoxymethyl-7-(3-fluoro-4 -methoxyphenyl)-1H-pyrazolo[3,4-g]quinoxaline (m.p. 179°–181° C.) and 2-carboethoxymethyl-7-(3-fluoro-4-methoxy-phenyl)-2H-pyrazolo[ 3,4-g]quinoxaline.

EXAMPLE 14

1-carboxymethyl-7-(3-fluoro-4-methoxyphenyl)-
1H-pyrazolo[3,4-g]quinoxaline 2-carboxymethyl-7-(3-fluoro-4-methoxyphenyl)-
1H-pyrazolo[3,4-g]quinoxaline 1-carboethoxymethyl-7-(3-fluoro-4-methoxyphenyl)-1H-pyrazolo[3,4-g]quinoxaline (0.3 g) is added to a solution of KOH (0.22 g) in 15 ml of methanol. The mixture is stirred at room temperature for 1½ hours then heated at 60° C. for 2 hours. The mixture is concentrated in vacuo and the residue is stirred in 20 ml of 0.5N aqueous HCl for ½ hour then the solid is filtered, washed with water and ether and air dried to obtain 1-carboxymethyl-7-(3-fluoro-4-methoxyphenyl)-1 H-pyrazolo[3,4-g]quinoxaline (m.p. >260° C.).

When the above procedure is followed and 1-carboethoxymethyl-7-(3-fluoro-4 -methoxyphenyl)-1H-pyrazolo[3,4-g]quinoxaline is replaced by 2-carboethoxymethyl-7-(3-fluoro-4-methoxyphenyl)-1H-pyrazolo[3,4-g]quinoxaline, then the product prepared is 2-carboxymethyl-7-(3-fluoro-4-methoxyphenyl)-1H-pyrazolo[3,4-g] quinoxaline.

EXAMPLE 15

1-cyanomethyl-7-(3-fluoro-4-methoxyphenyl)-
1H-pyrazolo[3,4-g]quinoxaline 2-cyanomethyl-7-(3-fluoro-4-methoxyphenyl)-
2H-pyrazolo[3,4-g]quinoxaline NaH (0.082 g) is added into a solution of 0.5 g of 7-(3-fluoro-4-methoxyphenyl)-1H-pyrazolo[ 3,4-g]quinoxaline and 10 ml of anhydrous DMF. The mixture is stirred for 15 minutes then 0.22 g of bromoacetonitrite is added into the mixture slowly. The resulting mixture is stirred at room temperature for 48 hours then poured into water. The product is collected by filtration, washed with water and air dried and purified by chromatography using 5%–20% of ethylacetate in methylene chloride as an eluent to obtain 1-cyanomethyl-7-(3-fluoro-4-methoxyphenyl)-1 H-pyrazolo[3,4-g]quinoxaline (m.p. 248°–252° C.) and 2-cyanomethyl-7-(3-fluoro-4-methoxyphenyl)-2H-pyrazolo[ 3,4-g] quinoxaline.

EXAMPLE 16

1-[2-hydroxyethyl]-7-(3-fluoro-4-methoxyphenyl)-
1H-pyrazolo[3,4-g]quinoxaline

To a mixture of 0.36 g of 1-(2-acetoxyethyl)-7-(3-fluoro-4-methoxyphenyl)-1 H-pyrazolo[3,4-g]quinoxaline in 50 ml of THF:MeOH:H$_2$O (3:1:1) is added 0.39 g of LiOH:H$_2$O and the resulting mixture is stirred at room temperature overnight. The MeOH and THF are removed in vacuo and the yellow crystalline solid precipitates out from the aqueous solution. More water is added to the mixture and cooled in an ice-bath for ½ hour. The product is collected by filtration, washed with water and air dried. The product is recrystallized from ethylacetate, collected and air dried to obtain 1-[2-hydroxyethyl]-7-(3-fluoro-4-methoxyphenyl)-1H-pyrazolo[3,4-g]quinoxaline (m.p. 192°–195° C.).

EXAMPLE 17

2-[2-hydroxyethyl]-6-(3-fluoro-4-methoxyphenyl)-
2H-pyrazolo[3,4-g]quinoxaline

When the procedure of Example 15 is followed and 1-(2-acetoxyethyl-7-(3-fluoro-4-methoxyphenyl)-1 H-pyrazolo[3,4-g]quinoxaline is replaced by 2-(2-acetoxyethyl-6-(3-fluoro-4-methoxyphenyl)-1H-pyrazolo[3,4-g]quinoxaline, then the product prepared is 2-[2-hydroxyethyl]-6-(3-fluoro-4-methoxyphenyl)-2H-pyrazolo[3,4-g]quinoxaline (m.p. 210°–212° C.).

EXAMPLE 18

1-[(4R)-2,2-dimethyl-[1,3]dioxolan-4-ylmethyl]-7
-(3-fluoro-4-methoxyphenyl)-1H-pyrazolo[3,4-g]
quinoxaline 2-[(4R)-2,2-dimethyl-[1,3]dioxolan-4-ylmethyl]-7
-(3-fluoro-4methoxyphenyl)-2H-pyrazolo[3,4-g]
quinoxaline NaH (0.08 g) is added to stirring solutions of 0.5 g of 7-(3-fluoro-4-methoxyphenyl)-1 H-pyrazolo[3,4-g]quinoxaline and 20 ml anhydrous DMF. After 10 minutes of stirring, 0.393 g of (R)-(–)-2,2-dimethyl-1,3-dioxalane-4-methanol mesylate is added into the mixture. The resulting mixture is stirred at room temperature for 2.5 hours then heated to gentle reflux for 2 hours. The mixture is poured into water and the precipitate is filtered, washed with water and air dried. The product is purified by silica-gel chromatography using 5%– 20% of ethylacetate in methylene chloride as eluent to obtain 1-[(4R)-2,2-dimethyl-[ 1,3]dioxolan-4-ylmethyl]-7-(3-fluoro-4-methoxyphenyl)-1H-pyrazolo[3,4-g] quinoxaline (m.p. 145°–151° C.) and 2-[(4R)-2,2-dimethyl-1,3]dioxolan-4 -ylmethyl]-7-(3-fluoro-4methoxyphenyl)-2H-pyrazolo[3,4-g]quinoxaline (m.p. 175°–179° C.).

EXAMPLE 19

1-[(2R)-1,2-dihydroxyprop-3-yl]-7-(3-fluoro-4
-methoxyphenyl)-1H-pyrazolo[3,4-g]quinoxaline 2-[(2R)-1,2-dihydroxyprop-3-yl]-7-(3-fluoro-4-
methoxyphenyl)-2H-pyrazolo-[3,4-g]quinoxaline A mixture of 0.24 g of 1-[(4R)-2,2-dimethyl-[1,3]dioxolan-4-ylmethyl]-7-(3 -fluoro-4-methoxyphenyl)-1H-pyrazolo[3,4-g]quinoxaline (0.05 g) of pyridinium p-toluenesulfonate and 20 ml of aqueous acetone (1:4H$_2$O:acetone) is heated to reflux overnight. The acetone is then removed in vacuo and the residue mixed with ether, filtered and the yellow solid is treated with saturated NaHCO₃, filtered, washed with water and air dried. This is recrystallized from ethylacetate, filtered and dried overnight. This is then recrystallized from CHCl₃ and the resultant product purified by column chromatography using 3% MeOH in methylene chloride to obtain 1-[(2R)-1,2-dihydroxyprop-3-yl)-7-(3-fluoro-4 -methoxyphenyl)-1H-pyrazolo-[3,4-g]quinoxaline (m.p. 228°–234° C.) and 2-[(2R)-1,2-dihydroxyprop-3-yl)-7 -(3-fluoro-4-methoxyphenyl)-2H-pyrazolo-[3,4-g]quinoxaline.

EXAMPLE 20

1-(2-piperdin-1-ylethyl)-7-(3-fluoro-4-methoxyphenyl)-1H-pyrazolo3,4-g]quinoxaline Step A 1-(2-tosyloxyethyl)-7-(3-fluoro-4-methoxyphenyl)-1H-pyrazolo[3,4-g]quinoxaline Pyridine (0.83 g) is added slowly to a mixture of 1-(2-piperdin-l-ylethyl)-7-(3-fluoro-4 -methoxyphenyl)-1H-pyrazolo[3,4-g]quinoxaline (1.42 g), p-tosylchloride (0.96 g) in 50 ml of anhydrous CH₂Cl₂. The resulting mixture is stirred at room temperature overnight. TLC shows reaction is going slowly so 2.6 eq. of Et₃N is added to the mixture and stirred overnight. The salt is filtered off, washed with CH₂Cl₂ and the filtrate is washed with water. The organic layer is separated, dried (Na₂SO₄), concentrated in vacuo which crystallized on standing. This is purified by chromatography using 5% ethylacetate/methylene chloride as eluent to obtain 1-(2-tosyloxyethyl)-7-(3-fluoro-4 -methoxyphenyl)-1H-pyrazolo[3,4-g]quinoxaline.

Step B 1-(2-piperdin-1-ylethyl)-7-(3-fluoro-4-methoxyphenyl)-1 H-pyrazolo[3,4-g]quinoxaline A mixture of 1-(2-tosyloxyethyl)-7-(3-fluoro-4-methoxyphenyl)-1H-pyrazolo[3,4-g]quinoxaline (0.3 g), piperdine (0.11 g) and 20 ml of anhydrous DMF is stirred at room temperature overnight. The mixture is heated to gentle reflux for 2½ hours. After cooling, it is poured into water and the precipitate is filtered, washed with water and air dried. This is then purified by chromatography using (3:7–1:9) methylene chloride in ethylacetate as eluent. 0.220 g of desired product to obtain 1-(2-piperdin-1-ylethyl)-7-(3-fluoro-4-methoxyphenyl)-1 H-pyrazolo[3,4-g]quinoxaline (m.p. 117°–120° C. (dec)).

EXAMPLE 21

When the procedures of the above examples are followed the following representative compounds may be prepared.
6-(3-fluorophenyl)-1H-pyrazolo[3,4-g]quinoxaline
7-(3-fluorophenyl)-1H-pyrazolo[3,4-g]quinoxaline
6-(3-chlorophenyl)-1H-pyrazolo[3,4-g]quinoxaline
7-(3-chlorophenyl)-1H-pyrazolo[3,4-g]quinoxaline
6-(3-bromophenyl)-1H-pyrazolo[3,4-g]quinoxaline
7-(3-bromophenyl)-1H-pyrazolo[3,4-g]quinoxaline
6-(3-trifluoromethylphenyl)-1H-pyrazolo[3,4-g]quinoxaline
7-(3-trifluoromethylphenyl)-1H-pyrazolo[3,4-g]quinoxaline
6-(3,5-dichlorophenyl)-1H-pyrazolo[3,4-g]quinoxaline
7-(3,5-dichlorophenyl)-1H-pyrazolo[3,4-g]quinoxaline
6-(3-methoxyphenyl)-1H-pyrazolo[3,4-g]quinoxaline
7-(3-methoxyphenyl)-1H-pyrazolo[3,4-g]quinoxaline
6-(4-methoxyphenyl)-1H-pyrazolo[3,4-g]quinoxaline
7-(4-methoxyphenyl)-1H-pyrazolo[3,4-g]quinoxaline
6-(3-ethoxyphenyl)-1H-pyrazolo[3,4-g]quinoxaline
7-(3-ethoxyphenyl)-1H-pyrazolo[3,4-g]quinoxaline
6-(3,4-dimethoxyphenyl)-1H-pyrazolo[3,4-g]quinoxaline
7-(3,4-dimethoxyphenyl)-1H-pyrazolo[3,4-g]quinoxaline
6-(3,5-dimethoxyphenyl)-1H-pyrazolo[3,4-g]quinoxaline
7-(3,5-dimethoxyphenyl)-1H-pyrazolo[3,4-g]quinoxaline
6-(2,6-dimethoxyphenyl)-1H-pyrazolo[3,4-g]quinoxaline
7-(2,6-dimethoxyphenyl)-1H-pyrazolo[3,4-g]quinoxaline
6-(2,5-dimethoxyphenyl)-1H-pyrazolo[3,4-g]quinoxaline
7-(2,5-dimethoxyphenyl)-1H-pyrazolo[3,4-g]quinoxaline
6-(3-fluoro-4-ethoxyphenyl)-1H-pyrazolo[3,4-g]quinoxaline
7-(3-fluoro-4-ethoxyphenyl)-1H-pyrazolo[3,4-g]quinoxaline
6-(3-chloro-4-methoxyphenyl)-1H-pyrazolo[3,4-g]quinoxaline
7-(3-chloro-4-methoxyphenyl)-1H-pyrazolo[3,4-g]quinoxaline
6-benzyl-1H-pyrazolo[3,4-g]quinoxaline
7-benzyl-1H-pyrazolo[3,4-g]quinoxaline
6-phenethyl-1H-pyrazolo[3,4-g]quinoxaline
7-phenethyl-1H-pyrazolo[3,4-g]quinoxaline
6-benzyloxy-1H-pyrazolo[3,4-g]quinoxaline
7-benzyloxy-1H-pyrazolo[3,4-g]quinoxaline
6-phenoxy-1H-pyrazolo[3,4-g]quinoxaline
7-phenoxy-1H-pyrazolo[3,4-g]quinoxaline
6-anilino-1H-pyrazolo[3,4-g]quinoxaline
7-anilino-1H-pyrazolo[3,4-g]quinoxaline
6-phenylthio-1H-pyrazolo[3,4-g]quinoxaline
7-phenylthio-1H-pyrazolo[3,4-g]quinoxaline
6-pyrid-2-yl-1H-pyrazolo[3,4-g]quinoxaline
7-pyrid-2-yl-1H-pyrazolo[3,4-g]quinoxaline
6-pyrid-3-yl-1H-pyrazolo[3,4-g]quinoxaline
7-pyrid-3-yl-1H-pyrazolo[3,4-g]quinoxaline
6-naphth-1-yl-1H-pyrazolo[3,4-g]quinoxaline
7-naphth-1-yl-1H-pyrazolo[3,4-g]quinoxaline
6-naphth-2-yl-1H-pyrazolo[3,4-g]quinoxaline
7-naphth-2-yl-1H-pyrazolo[3,4-g]quinoxaline
6-(N-methylbenzylamino)-1H-pyrazolo[3,4-g]quinoxaline
7-(N-methylbenzylamino)-1H-pyrazolo[3,4-g]quinoxaline
6-benzyloxymethyl-1H-pyrazolo[3,4-g]quinoxaline
7-benzyloxymethyl-1H-pyrazolo[3,4-g]quinoxaline
6-phenylthiomethyl-1H-pyrazolo[3,4-g]quinoxaline
7-phenylthiomethyl-1H-pyrazolo[3,4-g]quinoxaline
6-phenoxymethyl-1H-pyrazolo[3,4-g]quinoxaline
7-phenoxymethyl-1H-pyrazolo[3,4-g]quinoxaline
6-(2-methylphenyl)-1H-pyrazolo[3,4-g]quinoxaline
7-(2-methylphenyl)-1H-pyrazolo[3,4-g]quinoxaline
6-(3-methylphenyl)-1H-pyrazolo[3,4-g]quinoxaline
7-(3-methylphenyl)-1H-pyrazolo[3,4-g]quinoxaline
6-(4-methylphenyl)-1H-pyrazolo[3,4-g]quinoxaline
7-(4-methylphenyl)-1H-pyrazolo[3,4-g]quinoxaline
6-(2,4-dimethylphenyl)-1H-pyrazolo[3,4-g]quinoxaline
7-(2,4-dimethylphenyl)-1H-pyrazolo[3,4-g]quinoxaline
6-(3,4-dimethylphenyl)-1H-pyrazolo[3,4-g]quinoxaline
7-(3,4-dimethylphenyl)-1H-pyrazolo[3,4-g]quinoxaline
6-(3-cyanophenyl)-1H-pyrazolo[3,4-g]quinoxaline
7-(3-cyanophenyl)-1H-pyrazolo[3,4-g]quinoxaline
6-(4-cyanophenyl)-1H-pyrazolo[3,4-g]quinoxaline
7-(4-cyanophenyl)-1H-pyrazolo[3,4-g]quinoxaline
1-methyl-7-(thien-3-yl)-1H-pyrazolo[3,4-g]quinoxaline
2-methyl-7-(thien-3-yl)-2H-pyrazolo[3,4-g]quinoxaline
1-(2-methoxyethyl)-7-(thien-3-yl)-1H-pyrazolo[3,4-g]quinoxaline
2-(2-methoxyethyl)-7-(thien-3-yl)-2H-pyrazolo[3,4-g]quinoxaline
1-acetamido-7-(thien-3-yl)-1H-pyrazolo[3,4-g]quinoxaline
2-acetamido-7-(thien-3-yl)-2H-pyrazolo[3,4-g]quinoxaline
1-(pyrid-3-ylmethyl)-7-(3-fluoro-4-methoxyphenyl)-1H-pyrazolo[3,4-g]quinoxaline
2-(pyrid-3-ylmethyl)-7-(3-fluoro-4-methoxyphenyl)-2H-pyrazolo[3,4-g]quinoxaline 1-(pyrid-2-ylmethyl)-7-(3-fluorophenyl)-1H-pyrazolo[3,4-g]quinoxaline 2-(pyrid-2-ylmethyl)-7-(3-fluorophenyl)-2H-pyrazolo[3,4-g]quinoxaline 1-hydroxyethyl-7-(thien-3-yl)-1H-pyrazolo[3,4-g]quinoxaline 2-hydroxyethyl-7-(thien-3-yl)-2H-pyrazolo[3,4-g]quinoxaline 1-(2-N,N-diethylacetamido)-7-(3-fluoro-4-methoxyphenyl)-1H-pyrazolo[3,4-g]quinoxaline 2-(2-N,N-diethylacetamido)-7-(3-fluoro-4-methoxyphenyl)-2H-pyrazolo[3,4-g]quinoxaline 1-(3-thioproionamido)-7-(3-fluorophenyl)-1H-pyrazolo[3,4-g]quinoxaline 2-(3-thioproionamido)-7-(3-fluorophenyl)-2H-pyrazolo[3,4-g]quinoxaline 1-(3-carboxyethyl)-7-(3-fluorophenyl)-1H-pyrazolo[3,4-g]quinoxaline 2-(3-carboxyethyl)-7-(3-fluorophenyl)-2H-pyrazolo[3,4-g]quinoxaline 1-(2-N,N-dimethylaminoethyl)-7-(3-fluoro-4-methoxyphenyl)-1H-pyrazolo[3,4-g] quinoxaline 2-(2-N,N-dimethylaminoethyl)-7-(3-fluoro-4-methoxyphenyl)-2H-pyrazolo[3,4-g]quinoxaline

Preparation of Pharmaceutical Compositions and Pharmacological Test Section

Compounds within the scope of this invention exhibit significant activity as protein tyrosine kinase inhibitors and possess therapeutic value as cellular antiproliferative agents for the treatment of certain conditions including psoriasis, atherosclerosis and restenosis injuries. It is expected that the invention will be particularly applicable to the treatment of atherosclerosis. With regard to the treatment of some conditions, for example, atherosclerosis, certain people may be identified as being at high risk, for example, due to genetic, environmental or historical factors. Compounds within the scope of the present invention exhibit the modulation and/or inhibition of cell signaling, cell proliferation, cell inflammatory response, the control of abnormal cell growth and cell reproduction can and can be used in preventing or delaying the occurrence or reoccurrence of such conditions or otherwise treating the condition.

To determine the effectiveness of compounds of this invention, the following pharmacological tests described below, which are accepted in the art and recognized to correlate with pharmacological activity in mammals, are utilized. Compounds within the scope of this invention have been subjected to these various tests, and the results obtained are believed to correlate to useful cellular antiproliferative activity. The below described tests are useful in determining the EGF receptor kinase, PDGF receptor kinase and insulin receptor kinase inhibition activities of compounds disclosed herein. The results of these tests are believed to provide sufficient information to persons skilled in the pharmacological and medicinal chemistry arts to determine the parameters for using the studied compounds in one or more of the therapies described herein.

In order to test the present compounds for inhibition, the following procedure using PDGF stimulation is used. "$IC_{50}$," as used below refers to the concentration of inhibitor (mM) at which the rate of autophosphorylation is halved, compared with media containing no inhibitor.

Inhibition of PDGF-R Autophosphorylation

Lysate from NIH 3T3 cells was diluted one-third in Triton-free buffer and stimulated with 10 ng/ml PDGF for 30 minutes at 4° C. The equivalent of 1/15 of a 175. cm² plate of lysate was used per sample. The stimulated lysate was then immunoprecipitated with rabbit polyclonal anti-PDGF-receptor antibodies raised against a synthetic peptide from the COOH-terminal region (amino acids 1094–1106) or the human PDGF-receptor β-subunit and added to increasing concentrations of test compound of the present invention. After 10 minutes at 4° C., 10 µCi of [γ-$^{32}$P]ATP were added and further incubated for 10 minutes at 4° C. Samples were separated by SDS-PAGE on 6% gels.

Inhibition of Cell Proliferation as Measured by Inhibition of DNA Synthesis

EGF receptor overexpressing ($HER_{14}$) cells are seeded at $1\times10^5$ cells per well in 24-well Costar dishes pre-coated with human fibronectin (by incubating for 30 minutes at room temperature with 10 µg/0.5 ml/well). The cells are grown to confluence for 2 days. The medium is changed to DMEM containing 0.5 calf serum for 36–48 hour and the cells are then incubated with EGF (Toyobo, New York, N.Y.) (20 ng/ml), PDGF (Amgen) (20ng/ml) or serum (10% calf serum, FCS) and different concentrations of the compound of the present invention. [³H]thymidine, (NEN, Boston, Mass.) is added 16–24 hours later at 0.5 µCi/ml for 2 hours. TCA precipitable material is quantitated by scintillation counting (4° C.) Results of this assay are determined. "$IC_{50}$" of the concentration of inhibitor (nM) at which [³H]thymidine incorporation is halved, compare with media containing no buffer is calculated As FCS contains a broad range of growth factors, the $IC_{50}$ values for PDGF should be lower than for FCS, indicating that the compounds of the present invention do not act as general inhibitors.

These results of these tests indicate that compounds within the scope of the invention inhibit the PDGF growth factor receptors The following tables show examples of representative compounds of this invention and their test results as determined by the above inhibition of PDGF-R cell-free autophosphorylation procedure.

| COMPOUND | Inhibition of PDGF-R cell-free Autophosphorylation $IC_{50}(\mu M)$ |
|---|---|
| (structure with H-N-N, fused ring system, N, thiophene-Cl) | 2–10 |
| (structure with $H_3C-N$-N, fused ring system, N, thiophene-Cl) | 0.3 |

| COMPOUND | Inhibition of PDGF-R cell-free Autophosphorylation IC$_{50}$(μM) |
|---|---|
| [structure with OCH₃, F, H-N-N indazole, quinoxaline] | <0.02 |
| [structure with OCH₃, F, CH₃-N-N indazole, quinoxaline] | <2 |
| [structure with OCH₃, F, H-N-N(CH₃) indazole, quinoxaline] | <0.02 |

The results obtained by the above experimental methods evidence the useful protein tyrosine kinase inhibition properties of compounds within the scope of the present invention and possess therapeutic value as cellular antiproliferative agents. The above pharmacological test results may be used to determine the dosage and mode of administration for the particular therapy sought.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the for must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and if necessary, will be increased by small increments until the optimum effect under the circumstances is reached. The therapeutic human dosage, based on physiological studies using rats, will generally be from about 0.01 mg to about 100 mg/kg of body weight per day or from about 0.4 mg to about 10 g or higher although it may be administered in several different dosage units from once to several times a day. Oral administration requires higher dosages.

We claim:

1. A compound of the formula:

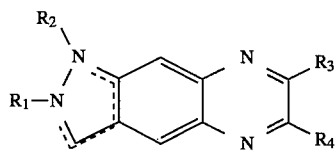

where:
- ------ may be a double bond;
- $R_1$ or $R_2$ is hydrogen, acyl, 1,2-dihydroxyethyl, 1,2-dihydroxyprop-3-yl, or

- $R_3$ or $R_4$ is Y—Ar the other being hydrogen;
- $R_5$ is hydrogen, alkyl, hydroxy, alkoxy, carboxy, carbalkoxy or carbamoyl;
- R is hydrogen or alkyl
- X is hydrogen, $C_4$–$C_6$ alkyl, alkenyl, hydroxy, 1,2-dihydroxyethyl, 1,2-dihydroxyprop-3-yl, alkoxy, carboxy, carbalkoxy, acyl, acyloxy, amino, mono- or di-alkyl-amino, acylamino, cyano, carbamoyl, acylcarbamoyl, mono- or di-alkylcarbamoyl, thiocarbamoyl, mono- or di-alkylthiocarbamoyl, acylthiocarbamoyl, 2,2-dialkyl-1,3-dioxolan-5-yl, 5-tetrazolyl, piperdinyl, pyridyl, phenyl or substituted phenyl where the substitution may be one or two groups independently selected from alkyl, alkoxy, carboxy, carbalkoxy, carbamoyl, mono- or di-alkylcarbamoyl, thiocarbamoyl, mono- or di-alkylthiocarbamoyl, halo or haloalkyl;
- Y is a bond, $(CH_2)_{1-3}$, $(CH_2)_nO(CH_2)_m$, $(CH_2)_nS(CH_2)_m$, or $(CH_2)_nNR(CH_2)_m$;
- n and m are independently 0–3 and n+m=0–3;
- x is 1–3;
- Ar is phenyl, substituted phenyl, thienyl, substituted thienyl, pyridyl, substituted pyridyl, α or β naphthyl or substituted α or β naphthyl where the substitution may be one or two groups independently selected from alkyl, hydroxy, alkoxy, halo, haloalkyl or cyano; or
- a pharmaceutically acceptable salt thereof.

2. A compound of claim 1 of the formula:

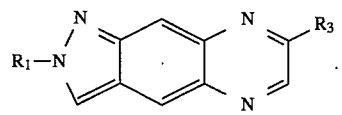

3. A compound of claim 1 of the formula:

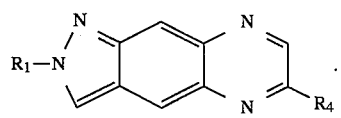

4. A compound of claim 1 of the formula:

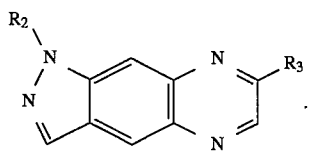

5. A compound of claim 1 of the formula:

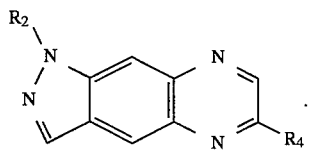

6. A compound of claim 2 of the formula:

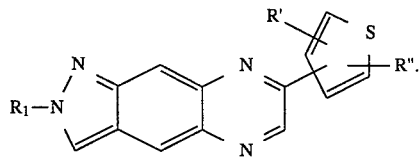

7. A compound of claim 2 of the formula:

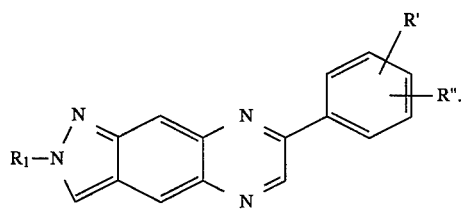

8. A compound of claim 3 of the formula:

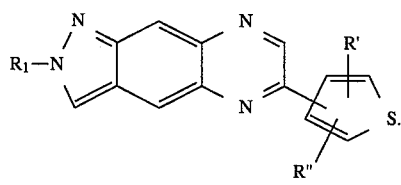

9. A compound of claim 3 of the formula:

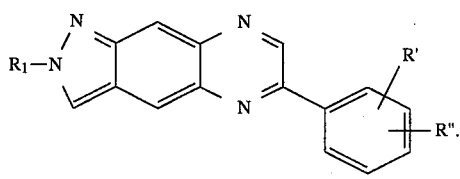

10. A compound of claim 4 of the formula:

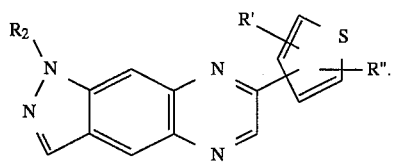

11. A compound of claim 4 of the formula:

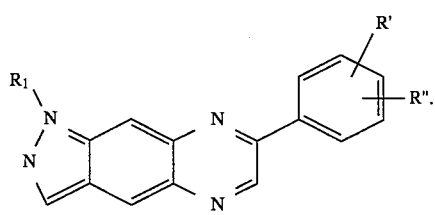

12. A compound of claim 5 of the formula:

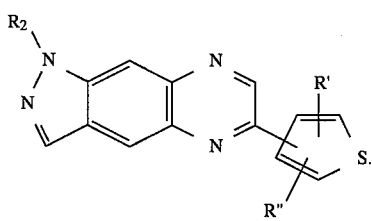

13. A compound of claim 5 of the formula:

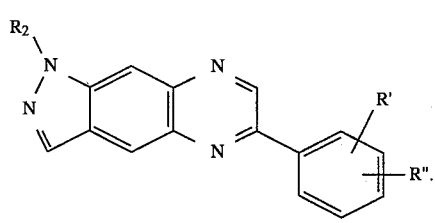

14. A compound of claim 6 of the formula:

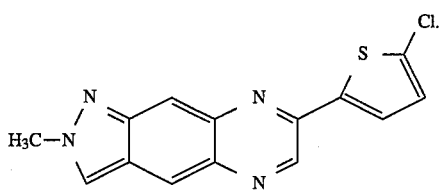

15. A compound of claim 7 of the formula:

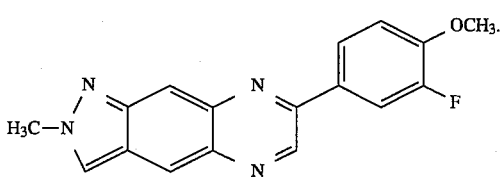

16. A compound of claim 11 of the formula:

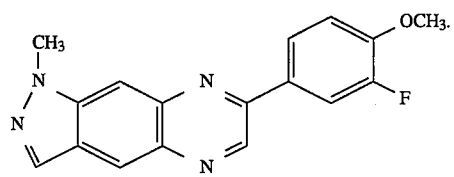

17. A compound of claim 11 of the formula:

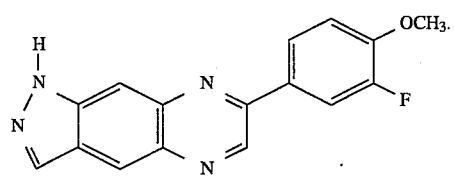

18. A compound of claim 11 of the formula:

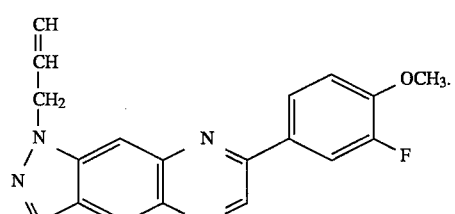

19. A compound of claim 11 of the formula:

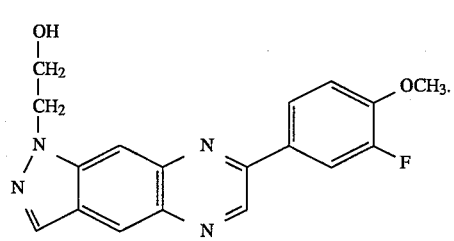

20. A compound of claim 11 of the formula:

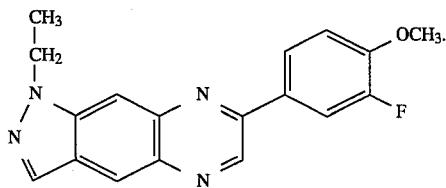

21. A compound of claim 11 of the formula:

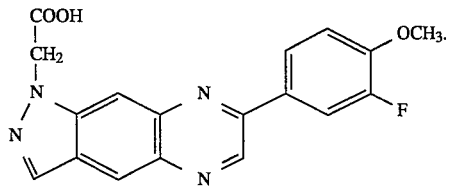

22. A compound of claim 7 of the formula:

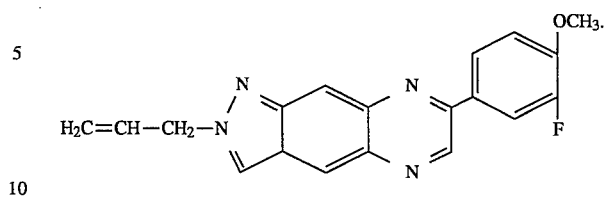

23. A pharmaceutical composition for inhibiting cell proliferation comprising a PDGF receptor inhibiting effective amount of a compound of claim 1 in admixture with a pharmaceutically acceptable carrier.

24. A method of inhibiting cell proliferation in a patient suffering from a disorder characterized by such proliferation comprising administering to a patient a pharmaceutical composition of claim 23.

* * * * *